United States Patent [19]

Bank et al.

[11] Patent Number: 5,623,083
[45] Date of Patent: Apr. 22, 1997

[54] ACETYLENIC ALCOHOLS AND ETHERS AS ACCELERATORS FOR HYDROSILATION OF SILOXYHYDRIDES

[75] Inventors: Howard M. Bank; Gary T. Decker, both of Midland, Mich.

[73] Assignee: Dow Corning Corporation, Midland, Mich.

[21] Appl. No.: 623,580

[22] Filed: Mar. 28, 1996

[51] Int. Cl.$^6$ ............................................. C07F 7/08
[52] U.S. Cl. ............................................. 556/479
[58] Field of Search ................................... 556/479

[56] References Cited

U.S. PATENT DOCUMENTS

| | | | |
|---|---|---|---|
| 2,823,218 | 2/1958 | Speier | 260/448.2 |
| 3,220,972 | 11/1965 | Lamereaux | 260/46.5 |
| 4,578,497 | 3/1986 | Onopchenko et al. | 556/479 |
| 5,359,111 | 10/1994 | Kleyer et al. | 556/479 |
| 5,449,802 | 9/1995 | Bank et al. | 556/479 |
| 5,486,637 | 1/1996 | Bank et al. | 556/479 |
| 5,493,045 | 2/1996 | Bank et al. | 556/479 |

*Primary Examiner*—Paul F. Shaver
*Attorney, Agent, or Firm*—William F. Boley

[57] ABSTRACT

A hydrosilation process where a siloxyhydride is reacted with an unsaturated reactant in the presence of a platinum catalyst and an accelerator selected from a group consisting of acetylenic alcohols and acetylenic ethers. The accelerators are especially useful for the hydrosilation of unsaturated reactants where the unsaturation is in the internal portion of the reactant's structure, for example, as in cyclopentene and cyclohexene.

23 Claims, No Drawings

ACETYLENIC ALCOHOLS AND ETHERS AS ACCELERATORS FOR HYDROSILATION OF SILOXYHYDRIDES

BACKGROUND OF INVENTION

The present invention is a hydrosilation process where a siloxyhydride is reacted with an unsaturated reactant in the presence of a platinum catalyst and an accelerator selected from a group consisting of acetylenic alcohols and acetylenic ethers. The accelerators are especially useful for the hydrosilation of unsaturated reactants where the unsaturation is in the internal portion of the reactant's structure, for example, as in cyclopentene and cyclohexene.

It is known in the art to produce organosilicon compounds by reacting a silicon hydride containing compound with an unsaturated organic compound in the presence of a catalyst. This reaction is typically referred to as hydrosilation or hydrosilylation. Typically the catalyst is platinum metal on a support, a platinum compound generally in a solvent, or a platinum complex.

In Speier et al., U.S. Pat. No. 2,823,218, a method for the production of organosilicon compounds by reacting an Si—H with a compound containing aliphatic carbon atoms linked by multiple bonds in the presence of chloroplatinic acid is taught. Lamoreaux, U.S. Pat. No. 3,220,972, teaches a similar process, however the catalyst is a reaction product of chloroplatinic acid.

One of the major problems known in the art with hydrosilation reactions is the de-activation of the catalyst prior to the completion of the reaction. One method for reactivation of the catalyst has been to expose the reaction mixture to oxygen. For example, Onopchenko et al., U.S. Pat. No. 4,578,497, teaches the use of an oxygenated platinum containing catalyst for use in hydrosilating alkylsilanes. Kleyer et al., U.S. Pat. No. 5,359,111, discloses a method for controlling hydrosilation reaction mixtures by controlling the solution concentration of oxygen in the reaction mixture, relative to the platinum present in the reaction mixture.

Bank et al., U.S. Pat. No. 5,449,802, disclose a hydrosilation process where a silicon hydride is reacted with an unsaturated reactant in the presence of a platinum catalyst and an accelerator selected from a group consisting of acetylenic alcohols, silated acetylenic alcohols, and acetylenic ethers.

In addition to the problem of de-activation of the platinum catalyst, hydrosilation processes taught in the art are not particularly effective in hydrosilating internal unsaturated bonds in organic molecules. The present inventors have unexpectedly discovered that acetylenic alcohols and acetylenic ethers can act as accelerators for platinum catalyzed hydrosilation of unsaturated reactants by siloxyhydrides. The accelerators are particularly effective in facilitating the hydrosilation of internal unsaturated bonds of organic molecules by siloxhydrides.

SUMMARY OF INVENTION

The present invention is a hydrosilation process where a siloxyhydride is reacted with an unsaturated reactant in the presence of a platinum catalyst and an accelerator selected from a group consisting of acetylenic alcohols and acetylenic ethers. The accelerators are especially useful for the hydrosilation of unsaturated reactants where the unsaturation is in the internal portion of the reactant's structure, for example, as in cyclopentene and cyclohexene.

DESCRIPTION OF INVENTION

The present invention is a hydrosilation process where a siloxyhydride is reacted with an unsaturated reactant in the presence of a platinum catalyst and a novel accelerator. The hydrosilation process comprises: contacting (A) a siloxyhydride described by formulas

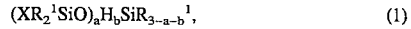 (1)

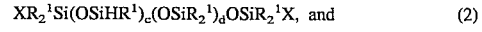 (2)

 (3)

where each $R^1$ is independently selected from a group consisting of alkyls comprising one to 20 carbon atoms, cycloalkyls comprising four to 12 carbon atoms, and aryls; each X is independently selected from a group consisting of hydrogen and $R^1$; a=0 to 4, b=0 to 3 with the proviso that when b=0 at least one X is hydrogen, a+b=1 to 4, c=0 to 100 with the proviso that when c=0 at least one X is hydrogen, d=0 to 100, c+d≦100, e=1 to 20, f=0 to 19, and e+f=4 to 20; and (B) an unsaturated reactant selected from a group consisting of (i) substituted and unsubstituted unsaturated organic compounds, (ii) silicon compounds comprising substituted or unsubstituted unsaturated organic substituents, and (iii) mixtures of (i) and (ii);

in the presence of a platinum catalyst selected from a group consisting of platinum compounds and platinum complexes, and an accelerator selected from a group consisting of acetylenic alcohols described by formulas

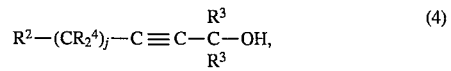 (4)

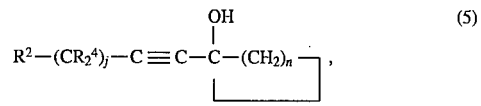 (5)

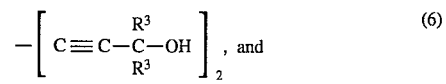 (6)

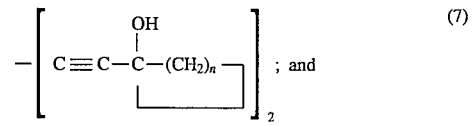 (7)

acetylenic ethers described by formulas

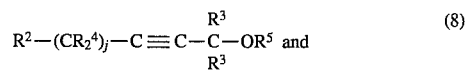 (8)

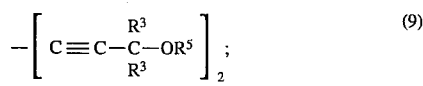 (9)

where $R^2$ is selected from a group consisting of hydrogen, hydroxyl, substituted and unsubstituted alkyls comprising one to 20 carbon atoms, and substituted and unsubstituted alkoxys comprising one to 20 carbon atoms, each $R^3$ is independently selected from a group consisting of hydrogen, alkyls comprising one to 20 carbon atoms, cycloalkyls comprising four to 20 carbon atoms, and aryls; each $R^4$ is independently selected from a group consisting of hydrogen and $R^1$, $R^5$ is selected from a group consisting of monovalent hydrocarbon radicals comprising one to 20 carbon atoms and heterocyclic hydrocarbon radicals having a carbon to oxygen bond, j=0 to 10, and n=4 to 12.

The contacting of the siloxyhydride with the unsaturated reactant can be effected in standard type reactors for conducting hydrosilation processes. The contact and reaction may be run as a continuous, semi-continuous, or batch reaction.

Siloxyhydrides which are useful in the present process are described by formulas (1), (2), and (3), where each $R^1$ is independently selected from a group consisting of alkyls comprising one to 20 carbon atoms, cycloalkyls comprising four to 12 carbon atoms, and aryls; each X is independently selected from a group consisting of hydrogen and $R^1$; a=0 to 4, b=0 to 3 with the proviso that when b=0 at least one X is hydrogen, a+b=1 to 4, c=0 to 100 with the proviso that when c=0 at least one X is hydrogen, d=0 to 100, c+d≦100, e=1 to 20, f=0 to 19, and e+f=4 to 20. $R^1$ can be a substituted or unsubstituted alkyl, cycloalkyl, or aryl as described.

In formulas (1), (2), and (3) it is preferred that each $R^1$ be independently selected from a group consisting of alkyls comprising about one to six carbon atoms. Even more preferred is when each $R^1$ is methyl. In formulas (1), (2), and (3) it is preferred that b=1, c+d=0 to 50, and e+f=4 to 7. Examples, of siloxyhydrides which may be useful in the present process include $HMe_2SiOSiMe_2H$, $HMe_2SiO(Me_2SiO)_{10}SiMe_2H$, $Me_3SiO(Me_2SiO)_3(HMeSiO)_5OSiMe_3$, $Me_3SiO(HMeSiO)_{35}SiMe_3$, $Si(OSiMe_2H)_4$, $(Me_3SiO)_2HSiMe$, and $PhSi(OSiMeH)_3$, where Me is methyl and Ph is phenyl. A preferred siloxyhydride is bis(trimethylsiloxy)methylsilane.

The siloxyhydride is contacted with an unsaturated reactant selected from a group consisting of (i) substituted and unsubstituted unsaturated organic compounds, (ii) silicon compounds comprising substituted and unsubstituted unsaturated organic substituents, and (iii) mixtures of (i) and (ii). For purpose of this invention, "unsaturated" means that the compound contains at least one carbon—carbon double bond.

More specific examples of the unsaturated reactants useful in the present process include unsubstituted cycloalkene compounds comprising at least four carbon atoms, substituted cycloalkene compounds comprising at least four carbon atoms, linear alkene compounds comprising about two to 30 carbon atoms, branched alkene compounds comprising four to about 30 carbon atoms, and mixtures of two or more of any of the above.

The substituted and unsubstituted cycloalkene compounds useful in the present process are those containing one or more unsaturated carbon—carbon bonds in the ring. The unsubstituted cycloalkene compounds may be, for example, cyclobutene, cyclopentene, cyclohexene, cycloheptene, cyclooctene, cyclopentadiene, 1,3-cyclohexadiene, and 1,3-cycloheptatriene. Substituted unsaturated compounds useful in the present invention may be, for example, 3-methylcyclopentene, 3-chlorocyclobutene, 4-phenylcyclohexene, and 3-methylcyclopentadiene. The preferred cycloalkene compounds are cyclohexene and cyclopentene, with cyclohexene being the most preferred.

Other unsaturated organic compounds useful in the present process are linear and branched alkenyl compounds including, for example, compounds with terminal unsaturation such as 1-hexene and 1,5-hexadiene, compounds with internal unsaturation such as trans-2-hexene, and unsaturated aryl containing compounds such as styrene and α-methylstyrene.

The unsaturated reactants may also comprise halogen, oxygen in the form of acids, anhydrides, alcohols, esters, and ethers; and nitrogen. Two or more of the above described unsaturated organic compounds may be used in the present process.

The unsaturated organic compounds comprising halogen may include, for example, vinyl chloride, allyl chloride, allyl bromide, allyl iodide, allyl bromide, methallyl chloride, trichloroethylene, tetrachloroethylene, tetrafluoroethylene, chloroprene, vinylidene chloride, and dichlorostyrene.

Suitable unsaturated organic compounds comprising oxygen can include, for example, ethers such as allyl and vinyl ethers; alcohols such as allyl alcohol (vinyl carbinol), methylvinylcarbinol and ethynyldimethyl-carbinol; acids such as acrylic, methacrylic, vinylacetic, oleic, sorbic, and linolenic; and esters such as vinyl acetate, allyl acetate, butenyl acetate, allyl stearate, methylacrylate, ethylcrotonate, diallyl succinate and diallyl phthalate. Suitable nitrogen containing unsaturated organic compounds include, for example, indigo, indole, acrylonitrile, and allyl cyanide.

Specifically included within the definition of unsaturated organic compounds are those substituted by organofunctional moieties such as $CH_2=CHCH_2OC(O)C(CH_3)=CH_2$, $CH_2=CHCH_2NHCH_2CH_2NH_2$, $CH_2=CHCH_2NH_2$,

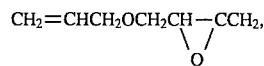

$CH_2=CHCH_2SH$, $CH_2=CHSi\{O(CH_2)_2OCH_3\}_3$, $CH_2=CHCH_2N(HCl)HCH_2CH_2NHCH_2(C_6H_4)CH=CH_2$, and other similar such compounds.

The unsaturated organic compound can be a silicon compound comprising substituted and unsubstituted organic substituents as described by, for example, formulas $(CH_2=CH(CH_2)_g)_hR^1_iSi(OR^1)_{4-h-i}$ and $(CH_2=CH(CH_2)_g)_hR^1_iSiCl_{4-h-i}$, where $R^1$ is as previously described, g=0 to 12, h=1 to 3, i=0 to 3, and h+i=1 to 4.

Prior to contact of the siloxyhydride with the unsaturated reactant, it may be preferable to treat or purify the unsaturated reactant. Methods useful for treating or purifying the unsaturated reactants are those known in the art for treating or purifying unsaturated organic compounds and include but are not limited to distillation and treatment with an adsorbent such as activated alumina or molecular sieves.

The relative amounts of siloxyhydride and unsaturated reactant used in the present process can be varied within wide limits. Although one unsaturated carbon—carbon linkage per silicon bonded hydrogen atom is stoichiometric, there is no requirement that the process be run under stoichiometric conditions. Preferred is when the process is run with from about zero to ten percent stoichiometric excess of silicon-bonded hydrogen atoms provided by the siloxyhydride.

The siloxyhydride and unsaturated reactant are contacted in the presence of a platinum catalyst selected from a group consisting of platinum compounds and platinum complexes. Any platinum containing material which effects the reaction between the siloxyhydride and an unsaturated carbon—carbon bond of the unsaturated organic compound is useful in the present invention. Examples of platinum catalysts useful in the present process are described, for example, in Onopchenko, U.S. Pat. No. 4,578,497; Lamoreaux, U.S. Pat. No. 3,220,972; and Speier, U.S. Pat. No. 2,823,218 all of which are hereby incorporated herein by reference.

The platinum catalyst can be, for example, chloroplatinic acid, chloroplatinic acid hexahydrate, Karstedt's catalyst (i.e. a complex of chloroplatinic acid with sym-divinyltetramethyldisiloxane), dichlorobis(triphenylphosphine)platinum(II), cis-dichlorobis(acetonitrile)platinum(II), dicarbonyldichloroplatinum(II), platinum chloride, and platinum oxide.

A preferred platinum catalyst is selected from the group consisting of chloroplatinic acid, chloroplatinic acid hexahydrate, and platinum vinylsiloxane complexes such as a neutralized complex of chloroplatinic acid or platinum dichloride with sym-divinyltetramethyldisiloxane.

Generally, those concentrations of platinum catalyst which provide at least about one mole of platinum per billion moles of unsaturated carbon—carbon bonds added to the process by the unsaturated reactant may be useful in the present process. Concentrations of platinum catalyst providing as high as about one mole of platinum per one thousand moles of unsaturated carbon—carbon bonds added to the process by the unsaturated reactant may be useful. Higher concentrations of platinum may be used if desired. A preferred concentration of platinum catalyst is that providing about one to 1000 moles of platinum per $1 \times 10^6$ moles of unsaturated carbon—carbon bonds provided to the process by the unsaturated reactant.

The platinum catalyst may be dissolved in a solvent for ease of handling and to facilitate measuring the small amounts typically needed. Suitable solvents include, for example, non-polar hydrocarbon solvents such as benzene, toluene, and xylene and polar solvents such as alcohols, ketones, glycols, and esters.

The present process is carried out in the presence of an accelerator selected from a group as described above by formulas (4) through (9). The substituent $R^2$ is selected from a group consisting of hydrogen, hydroxyl, substituted and unsubstituted alkyls comprising one to 20 carbon atoms, and substituted and unsubstituted alkoxys comprising one to 20 carbon atoms. Preferred is when $R^2$ is selected from a group consisting of hydrogen and alkyls comprising about one to about six carbon atoms. Substituent $R^2$ can be a substituted alkyl, for example, hydroxyethyl, 2-ethoxyethyl, and 1-methyl-1-hydroxyethyl. $R^2$ can be, for example, hydrogen, methyl, ethyl, propyl, iso-butyl, hydroxyethyl, 1-methyl-1-hydroxyethyl, and hexyl. Preferred is when $R^2$ is hydrogen. Each substituent $R^3$ is independently selected from a group consisting of hydrogen, alkyls comprising one to 20 carbon atoms, cycloalkyls comprising four to 20 carbon atoms, and aryls. $R^3$ can be, for example, hydrogen, methyl, ethyl, propyl, iso-butyl, cyclopentyl, cyclohexyl, and phenyl. Preferred is when each $R^3$ is independently selected from a group consisting of hydrogen, alkyls comprising one to six carbon atoms, and phenyl. Each substituent $R^4$ is an independently selected from a group consisting of hydrogen and $R^1$ as previously described. Preferred is when $R^4$ is hydrogen. $R^5$ is selected from a group consisting of monovalent hydrocarbon radicals comprising one to 20 carbon atoms and heterocyclic hydrocarbon radicals having a carbon to oxygen bond. $R^5$ can be, for example, alkyls such as methyl, ethyl, tert-butyl; cycloalkyls such as cyclopentyl and cyclohexyl; aryls such as phenyl and naphthyl; and heterocyclic hydrocarbons such as tetrahydrofuranyl.

In the acetylenic alcohols described by formulas (5) and (7), n can have a value of four to 12. Preferred is when n has a value of four or five.

In the acetylenic alcohols described by formulas (4), (5), and (8), j can have a value of zero to about ten. Preferred is when j is a value of zero to about four.

A preferred accelerator for use in the present process is 2-methyl-3-butyn-2-ol.

An effective concentration of the accelerator is added to the present process, where an effective concentration is one that facilitates initiation of the reaction between the silicon hydride and the unsaturated organic compound, accelerates the rate of the reaction, or reduces loss of reactivity of the catalyst in the process. A useful effective concentration of the accelerator is generally within a range of about 0.01 to 20 weight percent of the weight of the unsaturated reactant. Preferred is when the accelerator is about 0.1 to ten weight percent of the weight of the unsaturated reactant. The accelerator may be added to the process as a pre-mix with the platinum catalyst or separately.

The temperature at which the present process can be conducted can generally be within a range of about 40° C. to 220° C. It is preferred to conduct the process at a temperature within a range of about 50° C. to 170° C. The most preferred temperature for conducting the process is within a range of greater than 80° C. to about 150° C.

The following examples are provided to illustrate the present invention. These examples are not intended to limit the claims herein.

EXAMPLES

2-Methyl-3-butyn-2-ol was evaluated for the ability to accelerate the reaction of bis(trimethylsiloxy) methylsilane with cyclohexene in the presence of a platinum catalyst.

A stock mixture was prepared in an argon purged and blanketed bottle. The stock mixture comprised 8.2 g (0.1 mole) cyclohexene which had been treated with 13× molecular sieves and 19.4 g (0.1 mole) of bis(trimethylsiloxy)methylsilane. About $6 \times 10^{-5}$ moles of platinum, as a platinum divinylsiloxane complex, per mole of cyclohexene was added to the stock mixture. Aliquots (2 ml) of this catalyzed stock solution were then transferred to argon-purged glass tubes which contained 2-methyl-3-butyn-2-ol (MBO) at a concentration of about 0.4 volume percent based on the total volume of components added to the tube. The tubes were heat sealed under argon purge and heated either at 80° C. or 120° C. as described in Table 1 for three hours. At the end of three hours the tubes were cooled and the contents analyzed by gas chromatography using a thermal conductivity detector (GC-TC). The results of this analysis are reported in Table as the area percent of bis(trimethylsiloxy)cyclohexylmethylsilane ("Area % Bis-") under the GC-TC trace.

TABLE 1

| 2-Methyl-3-butyn-2-ol as Accelerator For Platinum Catalyzed Addition of Bis(trimethylsiloxy)methylsilane to Cyclohexene | | | |
|---|---|---|---|
| Example No. | MBO (μl) | Temp. (°C.) | Area % Bis- |
| 1 | — | 80 | 1.2 |
| 2 | 8 | 80 | 1.2 |
| 3 | — | 120 | 19.7 |
| 4 | 8 | 120 | 63.9 |

We claim:
1. A hydrosilation process comprising: contacting (A) a siloxyhydride described by formulas

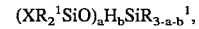

$(XR_2^1SiO)_aH_bSiR_{3-a-b}^1$,

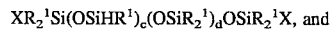

$XR_2^1Si(OSiHR^1)_c(OSiR_2^1)_dOSiR_2^1X$, and

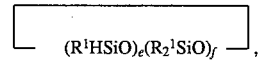

$\overline{(R^1HSiO)_e(R_2^1SiO)_f}$, where each $R^1$ is independently selected from a group consisting of alkyls comprising one to 20 carbon atoms, cycloalkyls comprising four to 12 carbon atoms, and aryls; each X is independently selected from a group consisting of hydrogen and $R^1$; a=0 to 4, b=0 to 3 with the proviso that when b=0 at least one X is hydrogen, a+b=1 to 4, c=0 to 100 with the proviso that when c=0 at least one X is hydrogen, d=0 to 100, c+d≦100, e=1 to 20, f=0 to 19, and e+f=4 to 20; and (B) an unsaturated reactant selected from a group consisting of (i) substituted and unsubstituted unsaturated organic compounds, (ii) silicon compounds comprising substituted or unsubstituted unsaturated organic substituents, and (iii) mixtures of (i) and (ii);

in the presence of a platinum catalyst selected from a group consisting of platinum compounds and platinum complexes, and an accelerator selected from a group consisting of acetylenic alcohols described by formulas $$R^2-(CR_2^4)_j-C\equiv C-\underset{R^3}{\overset{R^3}{C}}-OH,$$

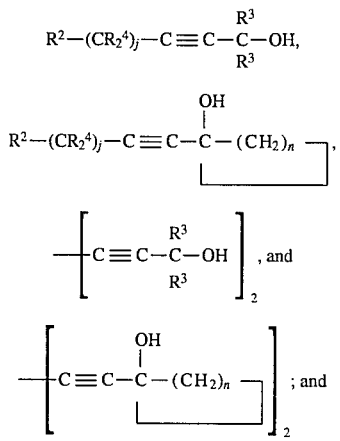

acetylenic ethers described by formulas $$R^2-(CR_2^4)_j-C\equiv C-\underset{R^3}{\overset{R^3}{C}}-OR^5 \text{ and}$$

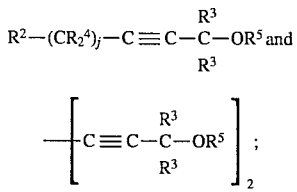

where $R^2$ is selected from a group consisting of hydrogen, hydroxyl, substituted and unsubstituted alkyls comprising one to 20 carbon atoms, and substituted and unsubstituted alkoxys comprising one to 20 carbon atoms, each $R^3$ is independently selected from a group consisting of hydrogen, alkyls comprising one to 20 carbon atoms, cycloalkyls comprising four to 20 carbon atoms, and aryls; each $R^4$ is independently selected from a group consisting of hydrogen and $R^1$; $R^5$ is selected from a group consisting of monovalent hydrocarbon radicals comprising one to 20 carbon atoms and heterocyclic hydrocarbon radicals having a carbon to oxygen bond, j=0 to 10, and n=4 to 12.

2. A process according to claim 1, where each $R^1$ is independently selected from a group consisting of alkyls comprising about one to six carbon atoms.

3. A process according to claim 1, where the siloxyhydride is bis(trimethylsiloxy)methylsilane.

4. A process according to claim 1, where the unsaturated reactant is selected from a group consisting of unsubstituted cycloalkene compounds comprising at least four carbon atoms, substituted cycloalkene compounds comprising at least four carbon atoms, linear alkene compounds comprising about two to 30 carbon atoms, and branched alkene compounds comprising four to about 30 carbon atoms.

5. A process according to claim 1, where the unsaturated reactant is selected from a group consisting of cyclohexene and cyclopentene.

6. A process according to claim 1, where the unsaturated reactant is cyclohexene.

7. A process according to claim 1, where the process is run with from about zero to 10 percent stoichiometric excess of silicon-bonded hydrogen atoms provided by the siloxyhydride relative to unsaturated carbon—carbon linkages of the unsaturated reactant.

8. A process according to claim 1, where the platinum catalyst is selected from a group consisting of chloroplatinic acid, chloroplatinic acid hexahydrate, and platinum divinylsiloxane complexes.

9. A process according to claim 1, where the platinum catalyst is a platinum divinylsiloxane complex.

10. A process according to claim 1, where the platinum catalyst is added to the process at a concentration which provides about one to 1000 moles of platinum per $1\times10^6$ moles of unsaturated carbon—carbon bonds provided to the process by the unsaturated reactant.

11. A process according to claim 1, where substituent $R^2$ of the accelerator is selected from a group consisting of hydrogen and alkyls comprising about one to six carbon atoms.

12. A process according to claim 1, where substituent $R^2$ of the accelerator is selected from a group consisting of hydrogen, methyl, ethyl, propyl, iso-butyl, 1-methyl-1-hydroxyethyl, and hexyl.

13. A process according to claim 1, where substituent $R^2$ of the accelerator is hydrogen.

14. A process according to claim 1, where each substituent $R^3$ of the accelerator is independently selected from a group consisting of hydrogen, alkyls comprising one to six carbon atoms, and phenyl.

15. A process according to claim 1, where substituent $R^5$ of the accelerator is selected from a group consisting of methyl, ethyl, tert-butyl, cyclopentyl, cyclohexyl, phenyl, naphthyl, and tetrahydrofuranyl.

16. A process according to claim 1, where the accelerator is 2-methyl-3-butyn-2-ol.

17. A process according to claim 1, where concentration of the accelerator is within a range of about 0.01 to 20 weight percent on the weight of the unsaturated reactant.

18. A process according to claim 1, where concentration of the accelerator is within a range of about 0.1 to ten weight percent of the weight of the unsaturated reactant.

19. A process according to claim 1, where the process is conducted at a temperature within a range of about 40° C. to 220° C.

20. A process according to claim 1, where the process is conducted at a temperature within a range of greater than 80° C. to about 150° C.

21. A process according to claim 1, where the siloxyhydride is described by formula $(XR^1_2SiO)_aH_bSiR^1_{3-a-b}$, $R^1$ is methyl, each X is independently selected from a group consisting of hydrogen and methyl, b=0 or 1 with the proviso that if b=0 at least one X is hydrogen, and a=0 to 4.

22. A process according to claim 1, where the siloxyhydride is described by formula $XR^1_2Si(OSiR^1H)_c(OSiR^1_2)_dOSiR^1_2X$, $R^1$ is methyl, each X is independently selected from a group consisting of hydrogen and methyl, c=0 to 50 with the proviso that if c=0 at least one X is hydrogen, and c+d=0 to 50.

23. A process according to claim 1, where the siloxhydride is described by formula

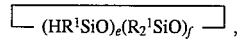

where $R^1$ is methyl and e+f=4 to 7.

* * * * *